United States Patent
Weintraub

(10) Patent No.: US 9,308,119 B2
(45) Date of Patent: *Apr. 12, 2016

(54) INTRAUTERINE DEVICE AND INSERTER FOR THE SAME

(71) Applicants: Jonathan Agmon, Herzliya Pituach (IL); Eran Soroker, Herzliya Pituach (IL); David Weintraub, Yavne (IL)

(72) Inventor: David Weintraub, Yavne (IL)

(73) Assignees: Jonathan Agmon, HerZliya Pituach (IL); David Weintraub, Yavne (IL); Eran Soroker, HerZliya Pituach (IL)

( * ) Notice: Subject to any disclaimer, the term of this patent is extended or adjusted under 35 U.S.C. 154(b) by 229 days.

This patent is subject to a terminal disclaimer.

(21) Appl. No.: 13/964,123

(22) Filed: Aug. 12, 2013

(65) Prior Publication Data

US 2013/0319424 A1 Dec. 5, 2013

Related U.S. Application Data

(62) Division of application No. 13/041,454, filed on Mar. 7, 2011, now Pat. No. 8,573,222.

(51) Int. Cl.
*A61F 6/18* (2006.01)
*A61F 6/14* (2006.01)

(52) U.S. Cl.
CPC .. *A61F 6/18* (2013.01); *A61F 6/144* (2013.01)

(58) Field of Classification Search
CPC ........................................................ A61F 6/18
USPC ......... 128/833, 832, 830, 834, 837, 838, 839, 128/840; 604/19, 48, 500, 506; 606/1, 53, 606/60, 246, 256, 252, 253
See application file for complete search history.

(56) References Cited

U.S. PATENT DOCUMENTS

| | | | | |
|---|---|---|---|---|
| 3,889,666 | A * | 6/1975 | Lerner | A61F 6/18 128/840 |
| 3,918,444 | A * | 11/1975 | Hoff | A61F 6/18 128/840 |
| 4,578,076 | A * | 3/1986 | Luukkainen et al. | 128/833 |
| 5,494,047 | A * | 2/1996 | Van Os | A61F 6/142 128/832 |
| 8,291,910 | B2 * | 10/2012 | de Graaff | A61F 6/14 128/833 |
| 8,573,222 | B2 * | 11/2013 | Weintraub | A61F 6/144 128/833 |
| 2004/0261799 | A1 * | 12/2004 | Mock | A61B 17/435 128/833 |

* cited by examiner

*Primary Examiner* — Victoria J Hicks
*Assistant Examiner* — Tarla Patel
(74) *Attorney, Agent, or Firm* — Soroker-Agmon

(57) ABSTRACT

An inserter for placing a T-shaped intrauterine device inside a patient's uterus and a T-shaped intrauterine device are disclosed. The inserter includes a sleeve part and a plunger part, the sleeve part includes a tube and a first engaging member and the plunger part includes a rod, a handle attached to the rod and a second engaging member. The first and the second engaging members are configured for reversibly engaging the sleeve part and the plunger part to temporarily lock the relative position between the tube and the rod. The T-shaped intrauterine device includes a pair of wings having a relaxed extended configuration and a contracted folded configuration and an elongated contraceptive body suspended from a junction between the wings.

8 Claims, 2 Drawing Sheets

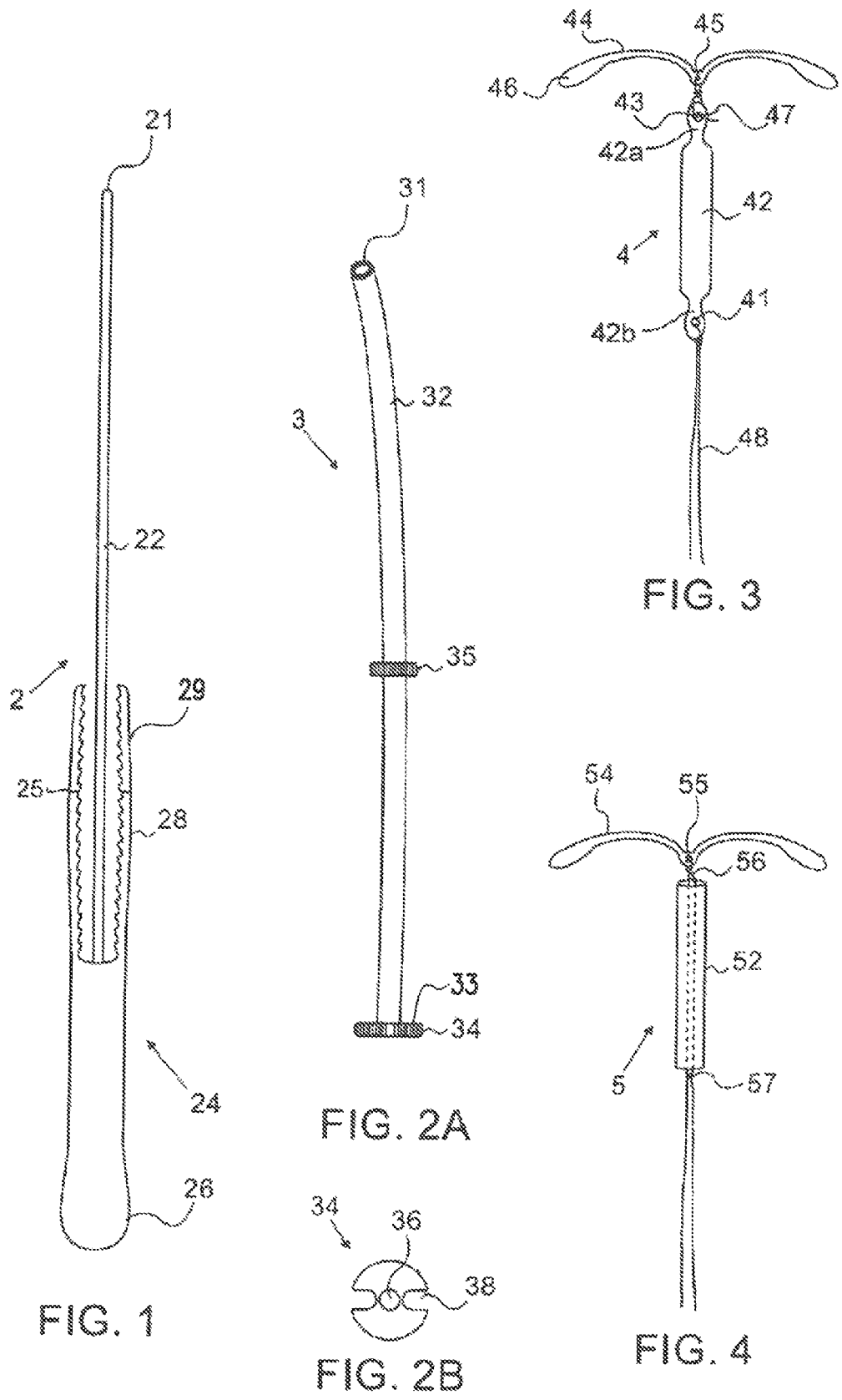

INTRAUTERINE DEVICE AND INSERTER FOR THE SAME

BACKGROUND OF THE INVENTION

1. Field of the Invention

The present invention generally relates to an intrauterine device (IUD) and to an inserter for placing the same. More specifically the invention relates to a combination of a one-hand-held inserter for positioning a T-shaped intrauterine device and to a T-shaped intrauterine device that are designed to make insertion easier while minimizing patient's discomfort and pain.

2. Discussion of the Related Art

Intrauterine devices and inserters for the same are well known. An intrauterine device (IUD) is a reversible, long acting, contraceptive device that is placed inside the uterus and can remain there for a few years. At any time that the woman plans to have a child, it can be easily removed by a clinician. Many women find the IUD to be very convenient because unlike oral contraceptives which require daily attention, an intrauterine device requires little action once it is in place.

Over the years various types of intrauterine devices have been proposed and applied. At present there are two types of IUDs in use: a copper-based IUD and a hormonal IUD. Copper-based IUDs are available in the T-framed shape or as frameless IUDs. The T-shaped IUDs comprise a T-shaped plastic frame having an elongated body partly wrapped by a copper coil and a pair of flexible transverse arms that hold the IUD in place near the top of the uterus. The IUD is inserted into the uterus with the transverse arms folded to facilitate the insertion through the cervical canal. Once the device is positioned inside the uterus, the arms are released and assume their transverse orientation. Depending on the particular device, the arms are either folded backward against the stem, as for example in TC-380A. (e.g., ParaGard®), or are folded in the forward direction against each other as in Nova-T type IUDs. The frameless copper IUD (e.g., GyneFix®) does not contain a T-shape frame but is a loop that holds several copper tubes and is anchored into the uterus fundus by a suture.

Of particular interest of the present invention are hormonal IUDs (also known as intrauterine system—IUS) which contain reservoir of hormone that is gradually released into the uterine cavity. At present there is only one hormonal IUD available for use, the T-frame LNG-20 distributed by Schering Og under the name Mirena®. It consists of a flexible plastic T-shaped frame surrounded by a hormone (levonorgestrel) cylinder. Hormonal IUDs have other benefits besides being contraceptive and may also be given for treatment of hormonal disorders and for hormone replacement therapy. Compared to copper-based IUDs such as for example the Nova-T, the LNG-20 is bulkier, having a body of larger diameter. Its insertion procedure requires more expertise and may be associated with more discomfort and pain to the patient.

The insertion and removal of an IUD is a medical procedure performed by a physician. The IUD is inserted through the cervix and into the uterine cavity by means of an inserter that typically includes an insertion tube that accommodates the IUD and a plunger. For T-shaped IUD the lateral arms are folded prior to insertion. An IUD typically also includes a string extending from its bottom end, which serves for monitoring the IUD and for facilitating its removal.

IUD is one of the most effective reversible contraceptive methods and has certain advantages over other birth control means with respect to cost-effectiveness and convenience, and because it is a long-term, reversible method, it can meet the needs of many women. However, despite these advantages, IUDs are widely used only in a few large countries, such as China, Egypt, and Vietnam, and are little used in most countries. In the United States, for example, only about 2% of women who use birth control means, use IUDs.

One of the reasons for IUDs not being more popular is the fear of the discomfort and pain associated with the insertion procedure. In addition, the general practice to perform insertion during the menstrual period may add to the discomfort felt by potential users. Further, although there is no minimum age for using IUD, it is often believed that IUDs should not be given to young women or to women who have never been pregnant.

There is therefore a continuous need to improve intrauterine devices and insertion procedure that may lead to greater acceptability and use of IUDs.

Accordingly, it is the general object of the invention to simplify IUD insertion procedure and to minimize the patient's discomfort and risk of complications during and after insertion.

In particular, it is an object of the present invention to provide an inserter for an intrauterine device that is easier to manipulate, that will make insertion procedure easier to the physician and less painful to the patient and that is simple to manufacture and to use.

It is another object of the present invention to provide an intrauterine device that is easier to insert and remove, that has a simple structure and is easy and inexpensive to manufacture.

SUMMARY OF THE PRESENT INVENTION

One aspect of the present invention is an inserter for placing a T-shaped intrauterine device inside a patient's uterus. The inserter comprises a sleeve part and a plunger part. The sleeve part comprises an open tube dimensioned to receive the contraceptive body of the intrauterine device and a first engaging member. The plunger part comprises a rod, a handle attached to one end of the rod and a second engaging member. The first and second engaging members are configured for reversibly and slidably engaging the sleeve part and the plunger part when the rod is inserted into the tube, and when the sleeve part and the plunger part are engaged, to temporarily lock the relative position between the tube and the rod. In accordance with an embodiment of the invention, the first engaging member comprises a disk attached to one open end of the tube, the disk having a central opening aligned with the open end and two opposite recesses and the second engaging member comprises two resilient arms dimensioned to be received in the two opposite recesses of the disk. The sleeve part and the plunger part can be separated into two separate parts.

Another aspect of the invention is a T-shaped intrauterine device comprising a transverse member and an elongated contraceptive body suspended from said transverse member. The transverse member comprises a pair of wings having a relaxed configuration in which the wings extended laterally and a contracted folded configuration in which the wings are folded against each other. Preferably the wings are convex. Optionally, the elongated contraceptive body is suspended from the transverse by means of a string connected to the junction zone between the two wings. Optionally, the string is threaded through an eyelet in the junction zone. The string may be connected to an eyelet at provided at one end of the elongated contraceptive body or may run along the central longitudinal axis of the elongated contraceptive body. Optionally the intrauterine device further comprises at least one removal string suspended from the bottom end thereof. The elongated contraceptive body may comprise a reservoir of at least one contraceptive agent and a sustained release means adapted for providing a sustained release of the contraceptive agent. The contraceptive agent may be a progesterone analog, e.g., levonorgestrel. Alternatively the elongated contraceptive body may comprise copper.

Yet, further aspects of the invention are a combination of the inserter and intrauterine device of the invention and a kit for the positioning of an intrauterine device inside a patient's uterus that includes the combination under sterile packaging.

BRIEF DESCRIPTION OF THE DRAWINGS

The present invention will be understood and appreciated more fully from the following detailed description taken in conjunction with the drawings in which:

FIG. 1 is a schematic side view of the plunger part of an inserter for positioning an intrauterine device, in accordance with an embodiment of the invention;

FIGS. 2A and 2B are side and bottom views, respectively, of the sleeve part of an inserter for positioning an intrauterine device, in accordance with an embodiment of the invention;

FIG. 3 is a schematic illustration of an intrauterine device in accordance with an embodiment of the invention;

FIG. 4 is a schematic illustration of an intrauterine device in accordance with another embodiment of the invention;

DETAILED DESCRIPTION OF THE PREFERRED EMBODIMENTS

Figures 5A, 5B, 5C:
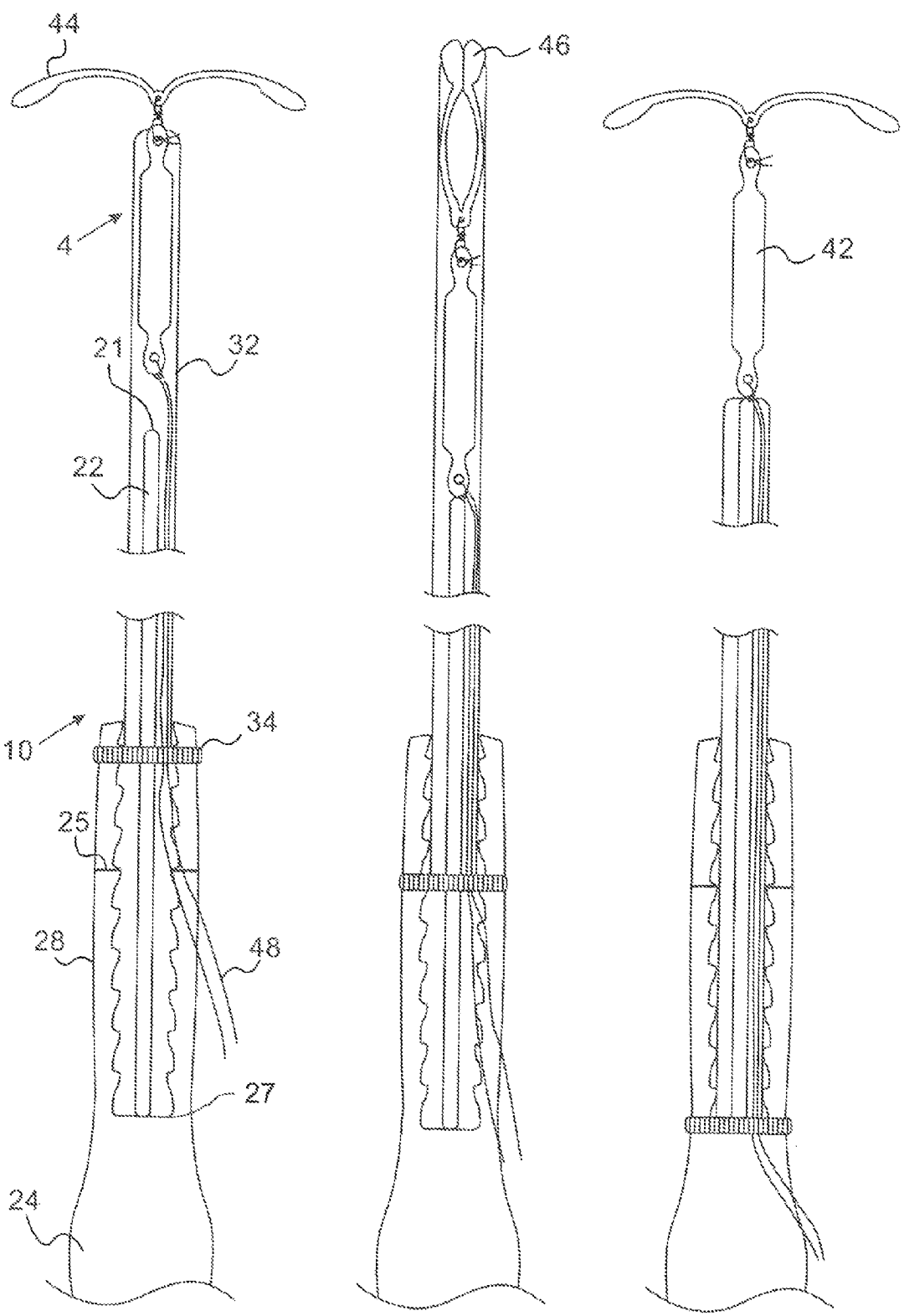
FIG. 5A is a broken view demonstrating the assembled inserter and the intrauterine device in a storage position.
FIG. 5B is a broken view illustration the intrauterine device and the inserter in a pre-inserting position.
FIG. 5C is a broken view illustrating the intrauterine device and the inserter after the intrauterine device is released from the inserter and before the inserter is withdrawn.

Referring to the drawings, FIGS. 1 and 2 depict the disassembled parts of an inserter for an intrauterine device in accordance with an embodiment of the invention. The assembled inserter, generally designated 10, is depicted in FIGS. 5A to 5C. Inserter 10 comprises a sleeve part 3 and a plunger part 2. Parts 2 and 3 can be easily assembled manually with no need for any tools and similarly can be easily disassembled into two separate parts to facilitate the removal of the inserter after the intrauterine device is positioned correctly inside the uterus.

Plunger part 2 comprises a thin rod 22 and a handle 24 fixedly attached to one end of the rod. Handle 24 comprises an elongated portion 26 to facilitate gripping by hand and two opposite resilient arms 28, a second engaging member 29, extending upwardly in the direction of and on opposite sides of rod 22, Arms 28 are configured as tweezers arms that can bend inwardly toward each other. Rod 22 and handle 24 are preferably made from a rigid sterilizable polymeric material such as polyethylene or the like. Rod 22, due to its small diameter/length ratio can easily flex to assume any curvature. Preferably part 2 is formed as a one integral piece, for example by mould injection. Alternatively, rod 22 can be attached to handle 24 by any other method including heat fusing, adhering and the like, or can be inserted into a bore drilled or otherwise formed in handle 24.

Sleeve part 3 comprises a tube 32 provided with a disk a first engaging member 33, at its proximal end. Tube 32 is a hollow tube made of medical grade sterilizable semi-rigid polymeric material such as polyethylene, polypropylene and the like. The inner diameter of the tube is dimensioned to receive the contraceptive body of a T-shaped intrauterine device, such as the devices depicted in FIGS. 3 and 4. The distal (upper) part of tube 32 is slightly curved to better adapt to the curvature of the uterus. The tube may be further bent before insertion and after examining the curvature of the uterus. Tube 32 may be further provided with a movable marking ring 35 which can slide along the tube. Ring 35 serves to mark the correct depth of insertion, i.e., the length of the uterine lumen, measured prior to insertion, as is well known in the art. Tube 32 may also include imprinted scaling marks (not shown) to facilitate positioning of ring 35. As shown in FIG. 2B, disk 34 comprises a central opening 36, substantially of the same diameter as the inner diameter of tube 32 and two opposite recesses 38. Recesses 38 are dimensioned to receive arms 28 of plunger 2.

Inserter 10 is assembled by inserting rod 22 of plunger 2 into tube 32 through opening 36 of disk 34 and forcing arms 28 of the plunger into recesses 34 of the disk, such that the tube can slide along the arms. As mentioned above, arms 28 are resilient and act like tweezers. When no pressure is applied on the arms, sleeve 3 can slide up and down arms 28 to assume any desired relative position between plunger and sleeve. When arms 28 are pressed against disk 36, the sleeve is locked to the plunger to maintain their relative position. Thus, disk 34 and arms 28 serve as engaging members that allow not only to easily assemble/disassemble the plunger and sleeve but also to easily lock/release their relative position. The inward surface of arms 28 may be smooth or may be toothed, as depicted in FIG. 1, to enhance the grip of disk 34 by arms 28. Alternatively, recesses 38 may be each provided with a small protrusion and arms 28 may be each provided with a complementary longitudinal slot running along the inward surface thereof for serving as a rail for sliding the disk along the arms (not shown).

In use, the inserter is held by one hand with portion 26 of handle 24 resting against the palm and arms 28 held between finger and thumb near the location of disk 34. When adjustment of the relative position of the tube and the rod is required in order to withdraw the IUD into the tube or to expose it, this can be easily done by gripping disk 36 between finger and thumb and sliding it axially along arms 28 in the required direction. When the relative position between tube and rod should be kept fixed, i.e., when the IUD is inserted through the cervix, the arms are pressed by finger and thumb against recesses 38 to lock sleeve 3 onto plunger 2, thus preventing possible relative movement between tube 32 and rod 21 and maintaining the IUD in its contracted configuration at the top of tube 32 as depicted in FIG. 5B. Arms 28 include markings 25 which mark the correct position of disk 34 when the inserter and IUD are ready for insertion.

It will be appreciated that the inserter of the present invention has the advantage of allowing the physician to manipulate both plunger and tube by one hand during the whole insertion procedure while leaving his other hand free to use other instruments or perform other operations as necessary. It will further appreciated that inserter 10 further allows for easily disengaging the plunger part from the sleeve part, thus allows withdrawal of the inserter, after the IUD is correctly placed, not as a whole unit, but by parts, namely first the plunger then the sleeve, to ensure that the monitoring string of the IUD is not entangled within the inserter and to reduce the risk of withdrawing the IUD along with the inserter.

Inserter 10 is designed for the insertion of a T-shaped IUD that comprises a cylindrical contraceptive body, i.e., copper-bearing or hormone releasing body, and a pair of foldable arms. Inserter 10 can be used for the insertion of any IUD of this type, including Nova-T and LNG-20 (Mirena®). However, in accordance with the general objective of the invention to make insertion easier while minimizing discomfort and pain, there is also provided a new IUD directed at this objective. The IUD of the invention, unlike known T-shaped frame IUDs, does not comprise a vertical stem that runs through the contraceptive body, but rather the contraceptive body is suspended from the middle node between the two transversal arms. The elimination of a central shaft allows for reducing the diameter of the contraceptive body, making insertion easier. The absence of a central relatively rigid shaft further allows for greater flexibility of the body, resulting with reduced bleeding and pain.

FIGS. 3 and 4 depict two embodiments designated 4 and 5, respectively, of an intrauterine device of the invention. Both embodiments comprise a pair of foldable resilient wings 44, 54 and a contraceptive body 42, 52 suspended from the junction zone between the two wings. Wings 44, 54 are of substantially similar shape as of those of the Nova-T and Mirena® devices. The wings are made of one resilient piece having a junction zone from which the two convex wings divert. In their expanded relaxed configuration, the wings are generally directed at opposite lateral directions substantially perpendicularly to the elongated body and having their tips 46 directed downward. The wings can easily flex toward each other around the junction where they meet and can reach a full contracted configuration to abut each other, as in FIG. 5B. Tips 46 are of substantially hemispherical shape forming a rounded leading end when the wings are pressed against each other in the contracted configuration. Preferably tips 46 are dimensioned to be slightly wider than opening 31 of tube 32 such that when the IUD is withdrawn into tube 32 they stop the RID at the correct position and prevent it from being withdrawn deeper into the tube. The structure and flexibility of the wings insures that the device can easily adapt to the lateral dimensions of the uterus and can easily respond to uterus contractions while minimizing the pressure applied on the uterus walls. In accordance with the embodiments shown in FIGS. 3 and 4, the wings comprise an eyelet 45, 55, respectively, in the junction zone between the wings.

In the embodiment depicted. FIG. 3, body 42 is provided with two extensions 42a and 42b at the upper and bottom ends, respectively, which comprise eyelets 43 and 41. In accordance with this embodiment, wings 44 and body 42 are connected by a flexible string 47 which is threaded first through one of eyelets 45 and 43 and is tied to form a first knot, then is threaded and tied around the second eyelet to form a second knot and loop. The ends of the string can be cut close to the knots. A second string 48 is tied to bottom eyelet 41. String 48 is used for monitoring the IUD and to facilitate its removal Body 42, which carries the contraceptive agent, may be a reservoir of contraceptive compound such as levonorgestrel or any other suitable progesterone analog. Body 42 may comprise a core of suitable polymeric matrix impregnated with the contraceptive agent and enveloped by a permeable membrane for controlling sustained release of the contraceptive agent into the uterus cavity over a prolonged time. Alternatively, body 42 may comprise a core enveloped with copper. Extensions 42a and 42b of body 42 may be formed as part of the envelope. It will be appreciated that body 42 may contain other or additional active therapeutic agents for treating various conditions of the uterus.

In the embodiment depicted in FIG. 4, only one string 56 is used for both connecting wings 54 to body 52 and as the monitoring and removal string. In accordance with this embodiment string 56 is inserted through the body substantially along its central longitudinal axis and is tied around eyelet 55. String 56 is inserted through body 52 either through a pre-fabricated channel that runs from top to bottom or by forcing the string through the resilient body by means of a needle-like instrument. The two ends of the string extending from the bottom end of body 52 are tied close to the body and serve for monitoring and removing the IUD. In accordance with the embodiment shown here, both ends of the string are inserted through the body, however it will be easily realized that alternatively only one end of the string may be inserted through the body such that the two ends of the string are extending from the opposites ends of the body, one end is tied to the wings while the other end is tied on itself to form a knot close to the body and is left to serve as the removal string. Body 52 may be of the type described above in association with FIG. 3, or alternatively may comprise copper rings or copper wire surrounding the string.

FIGS. 5A to 5C demonstrate the relative position of the tube, plunger and the IUD during storage (5A); immediately before insertion (5B); and immediately after the IUD is positioned in the uterus and before the inserter in withdrawn (5C).

During storage, the intrauterine device and the inserter are kept as a kit under sterilized sealed packaging. The package is opened a short time before the insertion and only after examination to determine the size, position, and curvature of the uterus.

As depicted in FIG. 5A, the packaged kit preferably contains inserter 10 in the assembled configuration and with the contraceptive elongated body 42 of IUD 4 inside the forward end of tube 32, protected thereby. During storage, wings 44 must be stored in the expanded configuration in order to prevent fatigue which might cause the wings to lose their flexibility. If the IUD is retained in the tube with its wings folded for a prolonged period, permanent deformation might occur and the arms might not return to their expanded configuration when released from the tube. At this position, i.e., with the IUD body protected inside tube 32 and wings 44 outside tube 32, tube 32 is mounted near the free ends of arms 28 and the tip 21 of plunger rod 22 does not contact the IUD but is located at certain distance below it.

FIG. 2B demonstrates the inserter and the IUD ready for insertion. At this configuration, wings 44 are withdrawn into tube 32 to assume their contracted configuration and the tip of plunger rod 22 contacts the bottom end of the IUD. To achieve this configuration, disk 34, held between finger and thumb, is retracted on arms 28 toward the handle and/or the handle is pushed forward until disk 34 is positioned on marks 25. At this configuration the IUD is entirely housed within tube 32 but for tips 46 which are exposed, and is ready for insertion. As mentioned above, tips 46 stop the IUD from being withdrawn further into the tube.

To place the IUD, the inserter as configured in FIG. 5B is inserted through the cervical canal into the uterus while pressing arms 28 inwardly against disk 34 to maintain the IUD in its contracted configuration within tube 22. When the IUD is in the correct position it is released from tube 22 by retracting disk 34 backward along arms 28 until it reaches handle 24 and cannot be further moved. FIG. 5C illustrates the configuration of the IUD and the inserter after release. The distance between marks 25 and the bottom end 27 of arms 28 substantially equals the length of the IUD in its contracted configuration.

After the IUD is correctly placed inside the uterus, inserter 10 may be withdrawn. In accordance with the invention withdrawal of the device may be performed by first withdrawing the plunger part, then withdrawing the sleeve part. Such a procedure reduces the risk, that removal string 48 will get entangled between the sleeve and the plunger which might result in the IUD being displaced or accidentally removed along with the inserter. In order to remove the plunger, disk 34 may be held steady while handle 24 is pulled backward until arms 28 are released from the disk and the plunger can be removed. Thereafter the sleeve part may be withdrawn.

It will be realized that the inserter of the invention may be used for the insertion of any type of T-shaped IUD while the IUD of the invention may be positioned by means of any other suitable inserter. However, the combination of the novel inserter and IUD of the invention provides certain advantages with respect to ease and simplicity of insertion, such as smaller diameter and more frontal flexibility, as well as with respect to simplicity and cost of manufacturing.

It will be appreciated by persons skilled in the art that the present invention is not limited to what has been particularly shown and described hereinabove. Rather the scope of the present invention is defined only by the claims which follow.

The invention claimed is:

1. A combination of an intrauterine device (IUD) and an inserter for placing the intrauterine device inside a patient's uterus, comprising:

a T-shaped intrauterine device comprising an elongated contraceptive body and a transverse member comprising a pair of wings attached to one end of said body, said transverse member and said body are connected therebetween by a flexible element suspending said body from a junction zone between said wings, the intrauterine device has a relaxed configuration in which said wings are extended laterally and a contracted configuration in which said wings are folded against each other; and an inserter for positioning said T-shaped intrauterine device in the patient's uterus, the inserter comprising a sleeve part and a plunger part;

said sleeve part comprising a tube having two open ends and a first engaging member, said tube is dimensioned to receive said the intrauterine device in the contracted configuration through one of said two open ends; and said plunger part comprising a rod, a handle attached to one end of the rod and a second engaging member;

said first and second engaging members are configured for reversibly and slidably engaging said sleeve part and said plunger part when the rod is inserted through the other open end of the tube and to temporarily lock the relative position between the tube and the rod, wherein said sleeve part and said plunger part when disengaged can be separated into two separate parts and wherein said first engaging member comprises a disk attached to the other open end of the tube, the disk having a central opening aligned with said other open end and two opposite recesses, and wherein said second engaging member comprises two resilient arms dimensioned to be received in said two opposite recesses.

2. The combination of claim 1 wherein said elongated contraceptive body comprises a reservoir of at least one contraceptive agent and a sustained release means adapted for providing a sustained release of said at least one contraceptive agent.

3. The combination according to claim 1 wherein the flexible element is a string and the contraceptive body is suspended by means of the string connected to the junction zone between the two wings.

4. The combination according to claim 3 wherein said string is connected to said one end of the elongated contraceptive body.

5. The combination according to claim 3 wherein said string is running along a central longitudinal axis of said elongated contraceptive body.

6. The combination of claim 1 wherein the IUD further comprises at least one removal string suspended from the bottom end of the contraceptive elongated body.

7. A kit for the positioning of an intrauterine device inside a patient uterus, the kit comprising the combination of claim 1 under sterile packaging.

8. An inserter for positioning a T-shaped intrauterine device in a patient's uterus, the inserter comprising a sleeve part and a plunger part;

said sleeve part comprising a tube having two open ends and a first engaging member, said tube is dimensioned to receive said elongated contraceptive body of the intrauterine device through one of said two open ends; and said plunger part comprising a rod, a handle attached to one end of the rod and a second engaging member;

said first and second engaging members are configured for reversibly and slidably engaging said sleeve part and said plunger part when the rod is inserted through the other open end of the tube and to temporarily lock the relative position between the tube and the rod, wherein said first engaging member comprises a disk attached to the other open end of the tube, the disk having a central opening aligned with said other open end and two opposite recesses, and wherein said second engaging member comprises two resilient arms dimensioned to be received in said two opposite recesses and operable akin to tweezers so that when the two resilient arms are pressed in the recesses against the disk the sleeve part is releasably locked onto the rod of the plunger part to maintain the relative position of the sleeve part and the plunger part, where the sleeve part releasable from the locking by relieving the pressure on the two resilient arms, and wherein said sleeve part and said plunger part when disengaged can be separated into two separate parts.

* * * * *